United States Patent [19]

Yoshida

[11] Patent Number: Plant 7,741

[45] Date of Patent: Dec. 10, 1991

[54] AFRICAN VIOLET NAMED 'ALYCE'

[76] Inventor: Eiichi Yoshida, P.O. Box 4836, Hayward, Calif. 94540-4836

[21] Appl. No.: 524,123

[22] Filed: May 14, 1990

[51] Int. Cl.[5] ..... A01H 5/00

[52] U.S. Cl. ..... Plt./69

[58] Field of Search ..... Plt./69

[56] References Cited

U.S. PATENT DOCUMENTS

P.P. 6,850 6/1989 Holtkamp ..... Plt. 69

*Primary Examiner*—James R. Feyrer

[57] ABSTRACT

A new variety of African violet plant for potted plant culture particularly distinguished by its year 'round blooming capability, its profuse production of flowers with ruffled edges, and its compact growth with abundant foliage of solid green color which provides a spreading base and attractive backing for the clusters of blossoms.

1 Drawing Sheet

BACKGROUND OF THE NEW PLANT

This new variety of African violet plant was obtained by cross-pollenating the seed parent "Melodie" Rhonda and the pollen parent "Melodie" Farrah×"Melodie" Julianne Sport. The seed pods of the pollenated plants were used as the generic basis for initiating further propagation trials. Seeds from the indicated cross were planted and germinated into a total of 1,368 plants. Of this total, 90 specimens appeared to be promising and were selected for further observation and testing vigor, earliness, and disease resistance as well as other desireable characteristics.

The plant of this disclosure was selected from the remaining selections of the original cross based on a number of outstanding characteristics in combination. Among the desireable traits of this selection are the ability of this plant to grow into specimens of excellent balance between leaf, plant and flower parts which compliment one another in appearance. Leaves are of moderate size, generally flat aspect, and borne by strong petioles of moderate length and with reddish coloration. Flowers are well placed above the expanse of the foliage and carried on strong peduncles which are well spaced from one another above the central portion of the plant's rosette. Elegant flowers of strong, uniform light purple hue, which does not fade and which open in uniformly spaced placement over the top central portion of the plant and are formed of five primary petals that mature into generally flat, full, rounded shape. Blooming season is extended by a good mix of open blooms and forming buds of uneven maturity. Few petaloids are presented; and are of the same color as petals but of smaller and of inconsistant size, and do not usually cover the bright yellow anthers.

In recognition of this plant's potential, it was denominated 'Alyce' and selected for introduction. I have asexually reproduced 'Alyce' by taking leaf cuttings to multiply the plant and form clonal specimens by procedures generally practiced in propagating *Saintpaulia ionantha* by those skilled in the art. Plants resulting from the original plant have been identical to the original selection in all distinguishing traits, and have established that the variety is stable.

BRIEF DESCRIPTION OF THE DRAWING

Sheet one is a full color photographic view of the plant in bloom, the colors shown being as nearly true as it is reasonably possible to obtain by conventional photographic procedures.

DESCRIPTION OF THE PLANT

The following is a detailed description of my new African violet with the color designation being accorded to The R.H.S. Colour Chart published by The Royal Horticultural Society of London, England, with collaboration by The British Colour Council.

THE PLANT

Name: Alyce.

Origin: Seedling.

Parentage:

*Seed parent.*—Saintpaulia Melodie Rhonda.

*Pollen parent.*—Saintpaulia Farrah×Saintpaulia Melodie Julianne Sport.

Classification:

*Botanic.*—*Saintpaulia ionantha.*

*Commercial.*—African violet.

Form: Rosette arrangement.

Height: 8 to 10 cm.

Growth: Moderate, petioles at first upright, becoming horizontal with age.

Size: Medium, to 22 cm. in diameter.

Mutation prone: None observed for flowers or foliage.

Foliage:

*Shape.*—Ovate, slight cordate base, rounded tip, slight crenate margin.

*Length.*—7 to 8 cm. on mature leaves.

*Width.*—6 to 7 cm. on mature leaves.

*Color.*—Upperside: Medium green. Underside: Pale green.

*Texture.*—Upperside: Thickly pubescent. Underside: Puberulent.

*Ribs and veins.*—Pronounced, pinnate, red pigmented on underside.

*Petiole.*—Flattened above, pubescent, pale green.

THE FLOWER

Blooming habit: Continuous and abundant under optimal growing conditions.
Number: Nine to twelve per peduncle.
Size of flower: Each flower is approximately 3 to 4 cm. in diameter.
Color: Purple, R.H.S. 78A.
Type: Single, violet-like.
Petals: Five per individual flower with ruffled margins.
Texture: Smooth, slightly flexible.
Appearance: Upperside glabrous, lowerside slightly puberulent.
Peduncles: Quinquepartite, red pigmented, puberulent.
Persistence: Flowers do not drop.
Fragrance: None.

REPRODUCTIVE ORGANS

Stamen: Two per flower.

*Anthers.*—Bright yellow, basifixed, two per filament.
*Filaments.*—c. 0.3 cm. in length.
*Pollen.*—Light yellow.
Pistils: One per flower.
*Stigma.*—Visible and accessible, becoming swollen when receptive and exuding a droplet of clear liquid.
*Style.*—c. 0.6 cm. in length.
*Ovary.*—Superior.

I claim:

1. A new and distinct cultivar of African violet named 'Alyce', as described and illustrated, and particularly characterized by its single, delicate, purple flower with slightly ruffled margin, and its year 'round blooming capacity which gives the plant a substantially continuous beauty.

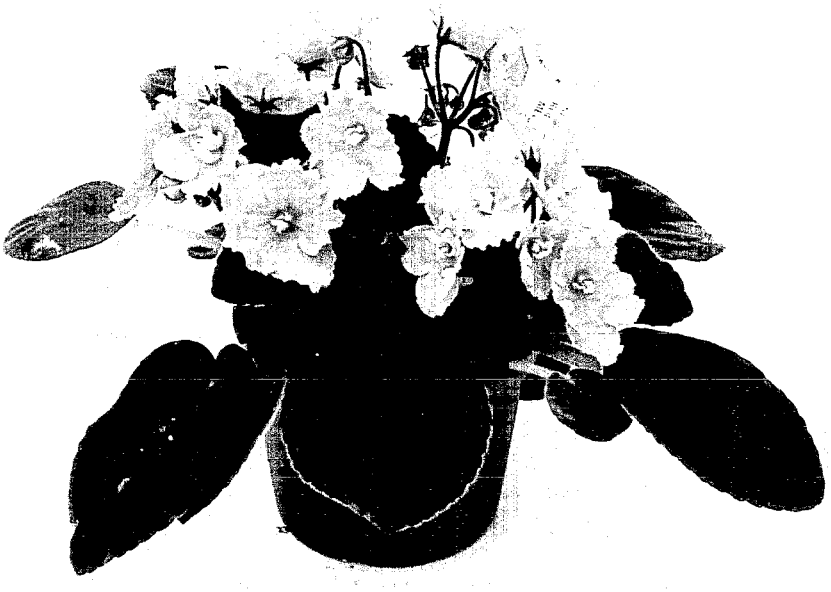

* * * * *